United States Patent [19]
Nitta et al.

[11] Patent Number: 5,702,519
[45] Date of Patent: Dec. 30, 1997

[54] FLAKY ALUMINUM OXIDE AND PEARLESCENT PIGMENT, AND PRODUCTION THEREOF

[75] Inventors: Katuhisa Nitta; Tan Ming Shau; Jun Sugahara, all of Fukushima-ken, Japan

[73] Assignee: Merck Patent Gesellschaft mit ceschrankter Haftung, Darmstadt, Germany

[21] Appl. No.: 710,252

[22] Filed: Sep. 13, 1996

[30] Foreign Application Priority Data

Sep. 14, 1995 [JP] Japan ................... 7-260959

[51] Int. Cl.⁶ ........................................ C09C 1/36
[52] U.S. Cl. ................. 106/442; 423/625; 424/401
[58] Field of Search ........................ 106/442, 312; 424/63, 69, 401, 484; 423/625

[56] References Cited

U.S. PATENT DOCUMENTS

| | | | |
|---|---|---|---|
| 3,926,660 | 12/1975 | Holle et al. | 106/300 |
| 4,115,144 | 9/1978 | Chambers et al. | 106/300 |
| 4,376,655 | 3/1983 | Weber | 106/300 |
| 4,842,848 | 6/1989 | Saita et al. | 424/63 |
| 4,882,133 | 11/1989 | Saegusa | 423/335 |
| 4,882,143 | 11/1989 | Kadokura et al. | 424/59 |
| 5,066,530 | 11/1991 | Kadokura et al. | 428/98 |

FOREIGN PATENT DOCUMENTS 60-54916  3/1985  Japan.

*Primary Examiner*—Deborah Jones
*Assistant Examiner*—Amy M. Harding
*Attorney, Agent, or Firm*—Millen, White, Zelano, & Branigan, P.C.

[57] ABSTRACT

A flaky substrate which is characterized by a uniform small thickness, a smooth nearly colorless surface, a large aspect ratio, and a very little tendency toward crystal twinning and aggregation, is composed of aluminum oxide and titanium oxide. The flaky substrate is used to prepare an excellent pearlescent pigment.

13 Claims, No Drawings

FLAKY ALUMINUM OXIDE AND PEARLESCENT PIGMENT, AND PRODUCTION THEREOF

BACKGROUND OF THE INVENTION

The present invention relates to a new grade of flaky, e.g., platelet-shaped aluminum oxide which is composed of aluminum oxide and titanium oxide and also to a process for producing the same. The flaky aluminum oxide containing titanium oxide is characterized by its large aspect ratio (particle diameter/thickness) and low tendency toward crystal twinning and aggregation. The present invention also relates to a pearlescent pigment formed from such flaky aluminum oxide by coating with metal oxide. The pearlescent pigment is useful as a raw material for paints, plastics, inks, cosmetics, and glazes.

There is known a pearlescent pigment which is formed by coating a flaky substrate (such as mica flakes) with a metal oxide (such as titanium oxide) having a high refractive index. A substrate desirable for this kind of pigment is a stable synthetic substance, such as flaky iron oxide, flaky titanium oxide, and aluminum doped flaky iron oxide, which has been developed and put on the market recently.

For better pearlescence, the substrate is required to be uniformly thin flakes with a large aspect ratio (i.e., with a large diameter compared to thickness), which are extremely colorless and transparent and have good heat resistance and high mechanical strength in the flaky state.

Aluminum oxide with high hardness finds use as wear-resistant material, ceramic material, paint pigment, abrasive, etc. Attempts have been made to produce simple aluminum oxide in a flaky form which would have improved characteristic properties. Typical examples proposed so far are given below.

- α-Aluminum oxide in the form of hexagonal flakes, having a particle diameter greater than 10 μm and an aspect ratio (particle diameter/thickness) of 5–10. (Japanese Patent Laid-open No. 111239/1982)
- α-Aluminum oxide in the form of flakes, having an average particle diameter of 0.5–3 μm. (Japanese Patent Publication No. 72527/1992)
- α-a-Aluminum oxide in the form of hexagonal small plate single crystals, 0.1–2 μm thick and 2–20 μm in diameter, with the aspect ratio being 5–40. (Japanese Patent Laid-open No. 131517/1991)
- Aluminum oxide in the form of fine platelet-shaped particles of a hexagonal crystal system, with the plane perpendicular to the c axis grown into a plate. (Japanese Patent Laid-open No. 39362/1992)

It turned out, however, that these kinds of aluminum oxide are not suitable for use as the flaky substrate for pearlescent pigments because of excessively small particle diameters, small aspect ratios, strong tendency toward crystal twinning and aggregation, and poor dispersion in water. In addition, such aluminum oxide particles are difficult to coat with a metal oxide because they are poorly dispersible in water and are composed of aluminum oxide alone. Even if coating is possible, the resulting coated particles are nonuniform particles in terms of metal oxide diameter and liable to aggregation and merely assume a dull pearlescence. Consequently, they are not suitable for use as a substrate for pearlescent pigments. Moreover, the above-mentioned aluminum oxide particles have a disadvantage that they are usually produced by the hydrothermal process (as disclosed in Japanese Patent Laid-open No. 39362/1992) which needs an expensive high-pressure reactor.

SUMMARY OF THE INVENTION

The present invention addresses problems associated with the prior art technology mentioned above. The present invention provides flaky aluminum oxide (e.g., to be used as a substrate) which is characterized by a greater aspect ratio than the conventional one, uniform small thickness, smooth surface, almost complete colorlessness, and very little tendency toward crystal twinning and aggregation. The present invention also provides a pearlescent pigment prepared by coating said flaky substrate with a metal oxide, and a simple process for producing said flaky aluminum oxide.

The present invention discloses a new grade of flaky aluminum oxide having outstanding characteristic properties required of substrates for pearlescent pigments. The flaky aluminum oxide is composed of aluminum oxide (as a major constituent) and titanium oxide (as a minor constituent). It is prepared from a uniform aqueous solution of water-soluble aluminum salt and titanium salt by hydrolysis with an alkali carbonate aqueous solution, under co-existence of an aqueous solution containing alkali metal sulfate and phosphoric acid (or phosphate), drying by evaporation (dehydration by heating), and molten-salt treatment.

The first aspect of the present invention resides in flaky aluminum oxide which comprises therein titanium oxide, i.e., in intimate admixture. Preferably, the flaky aluminum oxide has an average particle diameter of about 5–60 μm, a thickness less than about 1 μm, and an aspect ratio (particle diameter/thickness) greater than about 20.

The second aspect of the present invention resides in a process for producing flaky aluminum oxide, said process comprising preparing (a) an aqueous solution of at least one water-soluble aluminum salt and at least one titanium salt and (b) an aqueous solution of at least one alkali carbonate in an amount approximately chemically equivalent to said water-soluble aluminum salt and titanium salt in said aqueous solution (a), uniformly dissolving alkali metal sulfate and phosphoric acid or a phosphate in either aqueous solution (a) or aqueous solution (b), mixing said aqueous solutions (a) and (b) to give a suspension or gel containing hydrolyzates, drying the suspension or gel by evaporation, and molten-salt treating the dried product by heating at preferably about 900°–1400° C. to give a solid product, which is finished by water washing, filtering, and drying.

The third aspect of the present invention resides in a process for producing flaky aluminum oxide, said process comprising steps of adding dropwise a solution of water-soluble aluminum salt and a solution of alkali carbonate simultaneously to water in such a way that the former is approximately chemically equivalent (i.e., stoichiometrically) to the latter, thereby forming a suspension of hydrated aluminum hydroxide, adding this suspension (or solids filtered out from this suspension) to an aqueous solution of alkali metal sulfate, adding to the resulting solution a titanium salt and phosphoric acid or a phosphate to give a suspension or gel containing hydrolyzates, drying the suspension or gel by evaporation, and molten-salt treating the dried product by heating at, e.g., about 900°–1400° C. to give a solid product, which is finished by water washing, filtering, and drying.

The fourth aspect of the present invention resides in a pearlescent pigment which comprises particles of said flaky aluminum oxide and metal oxide coating formed on the surface of said particles.

The fifth aspect of the present invention resides in a paint, plastic, ink, cosmetic, or glaze composition which comprises containing therein said flaky aluminum oxide or said pearlescent pigment.

As compared with conventional aluminum oxide flakes composed of aluminum oxide alone, the flaky aluminum oxide of the present invention has a larger particle diameter, a uniform smaller thickness, and a larger aspect ratio. In addition, it has a smooth surface and very little tendency toward crystal twinning and aggregation, which are outstanding characteristic properties required of the substrate. It may be coated with a metal oxide having a high refractive index to give a pearlescent pigment which takes on a good pearlescent gloss. This pearlescent pigment is suitable for plastics, paint, ink, cosmetics, and glazes.

The flaky aluminum oxide of the present invention is produced by the process explained in detail in the following.

Process 1

This process starts with preparation of two aqueous solutions (a) and (b). The aqueous solution (a) is prepared from water-soluble aluminum salt and titanium salt. The formed may be selected from a variety of aluminum salts, of which aluminum sulfate and aluminum nitrate are desirable because of their availability and handling properties. The titanium salt may be selected from titanium tetrachloride, titanium trichloride, titanium oxysulfate, and titanyl sulfate. The amount of titanium salt varies depending on the shape (particle diameter, thickness, and aspect ratio) of the desired product. It is usually 0.1–4.0 wt. %, preferably 0.5–3.0 wt. % (in terms of oxide) of the amount of aluminum oxide. It is theorized that the titanium salt prevents crystal twinning and aggregation during crystal growth in the molten-salt treatment, and that titanium facilitates adhesion of metal oxide to the flaky aluminum oxide (as a substrate) in the process of preparing a pearlescent pigment by coating the substrate with a metal oxide. Titanium salt in an amount less than 0.1 wt. % may not be enough to prevent crystal twinning and aggregation. Conversely, titanium salt in an amount more than 4.0 wt. % may prevent the formation of flaky shaped aluminum oxide. In preparing the solution (a), heating will promote the dissolution of the components. The optimal amount of titanium can be routinely determined.

The aqueous solution (b) is prepared from alkali carbonate in an amount approximately chemically (i.e., stoichiometrically) equivalent for neutralization and hydrolysis of the water-soluble aluminum salt and titanium salt in the aqueous solution (a). A desirable alkali carbonate is sodium carbonate and potassium carbonate.

To the aqueous solution (a) or (b) is added alkali metal sulfate (as a mineralizer) and phosphoric acid or a phosphate (collectively referred to as phosphoric compound hereinafter). It is possible to add the two components together to either (a) or (b) or to add each of them to (a) and (b) separately. It is important to ensure complete dissolution in the solutions (a) and (b).

Examples of the alkali metal sulfate (as a mineralizer) include sodium sulfate, potassium sulfate, and lithium sulfate. The first two are desirable because of availability. They may be used in combination with one another. The amount (in mol) of the mineralizer is preferably 1 to 5 times the amount of the water-soluble aluminum salt. With an amount less than specified above, the mineralizer may not fully produce the effect of molten-salt heat treatment and flaking. With an amount more than specified above, the mineralizer may be wasted without added effect of flaking and need a large amount of water for removal by washing in the subsequent steps.

The phosphoric compound may be any water-soluble compound selected from phosphoric acid, phosphates, condensed phosphoric acid, and condensed phosphates. Examples include phosphoric acid, sodium secondary phosphate, sodium primary phosphate, potassium secondary phosphate, potassium primary phosphate, ammonium phosphate, sodium pyrophosphate, potassium pyrophosphate, sodium tripolyphosphate, potassium tripolyphosphate, and ammonium tripolyphosphate. The phosphoric compound makes crystals flaky during molten-salt treatment by heating. An amount less than 0.1 wt. % may not produce thin flaky aluminum oxide as desired. An amount more than 2.0 wt. % may not produce added effect in reducing the thickness of flaky aluminum oxide. In preparing the solution (b), heating will promote the dissolution of the components.

The aqueous solutions (a) and (b) prepared as mentioned above are mixed together by stirring to effect hydrolysis. The mixing may be accomplished in the following manner (1) or (2).

(1) Simultaneous dropping. This method consists of adding dropwise the aqueous solutions (a) and (b) simultaneously to water such that the former is approximately equivalent to the latter.

(2) Simple addition. This method consists of adding the solution (a) to the solution (b) or vice versa with stirring. The resulting product is a suspension or gel containing a hydrolyzate.

Mixing by the method (1) or (2) gives rise to a suspension or gel containing hydrated aluminum oxide (in the form of fine particles), mineralizer, hydrated titanium oxide, and phosphoric compound, which are uniformly dispersed in the aqueous medium. The suspension or gel is subsequently dehydrated and dried by evaporation. In order to reduce the amount of heat necessary for drying, it is desirable that the aqueous solutions (a) and (b) be prepared from a minimum of water, e.g., the solutions are nearly saturated. Another way of achieving this objective is by heating the aqueous solutions (a) and (b), thereby concentrating the salts, before starting the above-mentioned method (1) or (2). In any event, the aqueous solutions (a) and (b) should preferably contain a sufficient amount of water to ensure complete dissolution. If either or both of the two solutions contain undissolved matter, their mixing results in incomplete hydrolysis which leads to a product which is not flaky and uniform due to twinning and aggregation. In other words, the aqueous solutions (a) and (b) should be uniformly dissolved ones. The thoroughly dehydrated product is subsequently heat-treated at, e.g., about 900°–1400° C. The resulting product was washed with water to remove free compounds (mainly sulfates) sticking to it. The washed product is finally dried. In this way there is obtained the desired flaky aluminum oxide.

Process 2

This process employs as a raw material aluminum hydroxide which has previously been prepared from the same materials as used in the first process mentioned above. The aluminum hydroxide is prepared by adding dropwise a solution of water-soluble aluminum salt and a solution of alkali carbonate simultaneously to water such that the alkali carbonate is approximately equivalent to the aluminum salt. The resulting suspension containing hydrated aluminum oxide (or the solid separated from the suspension by washing and filtration) is added to an aqueous solution of alkali metal sulfate as a mineralizer. (The amount of alkali metal sulfate should preferably be 1 to 5 times (in mol) the amount of water-soluble aluminum salt.) To the resulting solution are further added titanium salt and phosphate. (The amount of titanium salt should preferably be 0.1–4.0 wt. %, in terms of titanium oxide, of the amount of aluminum oxide. The amount of phosphate should preferably be 0.1–2.0 wt. %, in terms of $P_2O_5$, of the amount of aluminum oxide.) The resulting suspension is thoroughly dehydrated by evaporation in the same manner as used in the first process mentioned above. During the dehydration step, titanium salt remaining unhydrolyzed is thermally hydrolyzed. The dehydrated product is molten-salt heat-treated at preferably about 900°–1400° C. The resulting product is washed with water to remove free compounds (mainly sulfates) sticking to it. The washed product is finally dried. In this way, there is obtained the desired flaky aluminum oxide. The hydrated aluminum oxide used in this process may be replaced by commercially available alumina sol or aluminum oxide in the form of fine particles.

For investigation of its physical properties, the sample of flaky aluminum oxide prepared as mentioned above according to the present invention was examined by a scanning electron microscope. It was found to have an average particle diameter of 5–60 μm, a thickness smaller than 1 μm, and an aspect ratio greater than 20. It was also found to be free from crystal twinning and aggregation and readily dispersible in water.

The good dispersibility was proved by the fact that the sample of flaky aluminum oxide gave a streamline when it was dispersed and stirred in water. (A streamline is a lamellar streaked pattern produced by reflected rays from the surface of flaky particles suspending and flowing in a liquid.)

Chemical analysis of the flaky aluminum oxide suggests that it contains nearly as much titanium as the starting material contains and that it contains only a trace amount of phosphorus. Presumably, the phosphorus compound used in the process of the present invention produces the effect of rendering the aluminum oxide flaky but it is finally released and removed from the system. The phosphoric compound helps the metal oxide to adhere to the aluminum oxide particles in the subsequent step. A probable reason for this is that a trace amount of phosphorus modifies the surface properties of the aluminum oxide particles in the step of heat treatment.

Thus, the flaky aluminum oxide defined in the present invention is composed of aluminum oxide (as a major component) and titanium oxide (as a minor component).

The pearlescent pigment pertaining to the present invention is prepared by coating said flaky aluminum oxide (as a substrate) with a metal oxide (such as titanium oxide and zirconium oxide) having a high refractive index. The coating layer produces a silvery color tone or an interference color depending on the coating thickness. If the coating material is replaced by a colored metal oxide, such as iron oxide, the resulting pearlescent pigment will take on a reddish or blackish color.

Coating with a metal oxide may be accomplished by any known method, such as hydrolysis of a metal salt by heating or alkali, which deposits hydrated metal oxide, followed by calcination. If this calcination is carried out in a reducing atmosphere, the resulting pearlescent pigment takes on a blackish color due to titanium oxide or iron oxide in a lower oxidation state.

Coating with a metal oxide is difficult to perform on the conventional substrate, which is flaky aluminum oxide composed of aluminum oxide alone. By contrast, the flaky aluminum oxide pertaining to the present invention is highly receptive to a metal oxide. The resulting metal oxide coating is very thin and uniform and hence produces an excellent pearlescent gloss.

The flaky aluminum oxide pertaining to the present invention or the pearlescent pigment derived therefrom may be used as such as a raw material of ceramics or as a pigment for paint, plastics, ink, cosmetics, and glaze. Depending on its use, it will undergo treatment which imparts water resistance, weather resistance, chemical resistance, discoloration resistance, or high dispersibility.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding Japanese application 7-260959, filed Sep. 14, 1995, are hereby incorporated by reference.

EXAMPLES (Preparation of flaky aluminum oxide)

Example 1

In 450 ml of deionized water were dissolved 223.8 g of aluminum sulfate 18-hydrate, 114.5 g of anhydrous sodium sulfate, and 93.7 g of potassium sulfate, by heating up to about 75° C. To the resulting solution was added 2.0 g of 34.4% solution of titanyl sulfate. The resulting solution is designated as the aqueous solution (a).

In 250 ml of deionized water were dissolved 0.9 g of sodium tertiary phosphate 12-hydrate and 107.9 g of sodium carbonate. The resulting solution is designated as the aqueous solution (b).

The aqueous solutions (a) and (b) were added simultaneously to 200 ml of deionized water with stirring at a constant rate over about 15 minutes, in such a manner that the solutes in the solution (a) are approximately equivalent to the solutes in the solution (b). Stirring was continued for additional 15 minutes. The resulting solution was evaporated to dryness. The resulting solids were heated at approximately 1200° C. for 5 hours. Water was added to the heat-treated product to dissolve free sulfate. Insoluble solids were filtered off, washed with water, and finally dried. Thus, there was obtained the desired flaky aluminum oxide.

The thus obtained flaky aluminum oxide was examined by X-ray diffractometry. The diffraction pattern had only peaks attributable to aluminum oxide (corundum). It was found by chemical analysis that the flaky aluminum oxide contains titanium oxide in an amount of 0.9%. Observation by an optical microscope and an electron microscope revealed that the flaky aluminum oxide has a particle diameter of 3–16 μm and a thickness of about 0.2 μm and is free from crystal twinning. When dispersed into water by stirring, the flaky aluminum oxide produced a smooth streamline which is a sign of good dispersibility.

Example 2

In 300 ml of deionized water were dissolved 111.9 g of aluminum sulfate 18-hydrate, 57.3 g of anhydrous sodium sulfate, and 46.9 g of potassium sulfate, by heating to above 60° C. To the resulting solution was added 1.0 g of 34.4% solution of titanyl sulfate. The resulting solution is designated as the aqueous solution (a).

In 150 ml of deionized water were dissolved 0.45 g of sodium tertiary phosphate 12-hydrate and 54.0 g of sodium carbonate. The resulting solution is designated as the aqueous solution (b).

The aqueous solution (b) was added with stirring to the aqueous solution (a), which had been heated to about 60° C. Stirring was continued for 15 minutes. The resulting mixture of the two solutions was a gel. This gel was evaporated to dryness. The resulting solids were heated at approximately 1200° C. for 5 hours. Water was added to the heat-treated product to dissolve free sulfate. Insoluble solids were filtered off, washed with water, and finally dried. Thus, there was obtained the desired flaky aluminum oxide.

The thus obtained flaky aluminum oxide was examined by X-ray diffractometry. The diffraction pattern had only peaks attributable to aluminum oxide (corundum). It was found by chemical analysis that the flaky aluminum oxide contains titanium oxide in an amount of 0.9%. Observation by an optical microscope and an electron microscope revealed that the flaky aluminum oxide has a particle diameter of 4–21 µm and a thickness of about 0.2 µm and is free from crystal twinning. When dispersed into water by stirring, the flaky aluminum oxide produced a smooth streamline which is a sign of good dispersibility.

Example 3

In 300 ml of deionized water were dissolved 111.9 g of aluminum sulfate 18-hydrate, 57.3 g of anhydrous sodium sulfate, and 46.9 g of potassium sulfate, by heating to above 60° C. To the resulting solution was added 3.0 g of 34.4% solution of titanyl sulfate. The resulting solution is designated as the aqueous solution (a).

In 50 ml of deionized water were dissolved 0.45 g of sodium tertiary phosphate 12-hydrate and 55.0 g of sodium carbonate. The resulting solution is designated as the aqueous solution (b).

The aqueous solution (b) was added with stirring to the aqueous solution (a), which had been heated to about 60° C. Stirring was continued for 15 minutes. The resulting mixture of the two solutions was a gel. This gel was evaporated to dryness. The resulting solids were heated at 1200° C. for 5 hours. Water was added to the heat-treated product to dissolve free sulfate. Insoluble solids were filtered off, washed with water, and finally dried. Thus, there was obtained the desired flaky aluminum oxide.

The thus obtained flaky aluminum oxide was examined by X-ray diffractometry. The diffraction pattern had only peaks attributable to aluminum oxide (corundum). It was found by chemical analysis that the flaky aluminum oxide contains titanium oxide in an amount of 2.6%. Observation by an optical microscope and an electron microscope revealed that the flaky aluminum oxide has a particle diameter of 5–22 µm and a thickness of about 0.2 µm and is free from crystal twinning. When dispersed into water by stirring, the flaky aluminum oxide produced a smooth streamline which is a sign of good dispersibility.

Example 4

In 300 ml of deionized water were dissolved 111.9 g of aluminum sulfate 18-hydrate, 75.3 g of anhydrous sodium sulfate, and 46.9 g of potassium sulfate, by heating to above 60° C. To the resulting solution was added 1.0 g of 34.4% solution of titanyl sulfate. The resulting solution is designated as the aqueous solution (a).

In 150 ml of deionized water were dissolved 1.35 g of sodium tertiary phosphate 12-hydrate and 54.0 g of sodium carbonate. The resulting solution is designated as the aqueous solution (b).

The aqueous solution (b) was added with stirring to the aqueous solution (a), which had been heated to about 60° C. Stirring was continued for 15 minutes. The resulting mixture of the two solutions was a gel. This gel was evaporated to dryness. The resulting solids were heated at 1200° C. for 5 hours. Water was added to the heat-treated product to dissolve free sulfate. Insoluble solids were filtered off, washed with water, and finally dried. Thus, there was obtained the desired flaky aluminum oxide.

The thus obtained flaky aluminum oxide was examined by X-ray diffractometry. The diffraction pattern had only peaks attributable to aluminum oxide (corundum). It was found by chemical analysis that the flaky aluminum oxide contains titanium oxide in an amount of 0.8%. Observation by an optical microscope and an electron microscope revealed that the flaky aluminum oxide has a particle diameter of 5–20 µm and a thickness of about 0.2 µm and is free from crystal twinning. When dispersed into water by stirring, the flaky aluminum oxide produced a smooth streamline which is a sign of good dispersibility.

Example 5

In 300 ml of deionized water were dissolved 111.9 g of aluminum sulfate 18-hydrate, 57.3 g of anhydrous sodium sulfate, and 46.9 g of potassium sulfate, by heating to above 60° C. To the resulting solution was added 0.5 g of 34.4% solution of titanyl sulfate. The resulting solution is designated as the aqueous solution (a).

In 150 ml of deionized water were dissolved 0.45 g of sodium tertiary phosphate 12-hydrate and 53.7 g of sodium carbonate. The resulting solution is designated as the aqueous solution (b).

The aqueous solution (b) was added with stirring to the aqueous solution (a), which had been heated to about 60° C. Stirring was continued for 15 minutes. The resulting mixture of the two solutions was a gel. This gel was evaporated to dryness. The resulting solids were heated at 1100° C. for 5 hours. Water was added to the heat-treated product to dissolve free sulfate. Insoluble solids were filtered off, washed with water, and finally dried. Thus, there was obtained the desired flaky aluminum oxide.

The thus obtained flaky aluminum oxide was examined by X-ray diffractometry. The diffraction pattern had only peaks attributable to aluminum oxide (corundum). It was found by chemical analysis that the flaky aluminum oxide contains titanium oxide in an amount of 0.4%. Observation by an optical microscope and an electron microscope revealed that the flaky aluminum oxide has a particle diameter of 4–18 µm and a thickness of about 0.2 µm and is free from crystal twinning. When dispersed into water by stirring, the flaky aluminum oxide produced a smooth streamline which is a sign of good dispersibility.

Example. 6

In 500 ml of deionized water was dissolved 223.8 g of aluminum sulfate 18-hydrate by heating. In 250 ml of deionized water was dissolved 106.8 g of sodium carbonate. The two aqueous solutions were added simultaneously to 200 ml of deionized water with stirring at a constant rate over about 15 minutes, in such a manner that the solute in the first solution was always approximately equivalent to the solute in the second solution. Stirring was continued for additional 15 minutes. There was obtained a dispersion. The dispersion was filtered off and the solids were washed with water. Thus, there was obtained hydrated aluminum oxide.

In 500 ml of deionized water were dissolved 57.3 g of anhydrous sodium sulfate and 46.9 g of potassium sulfate by heating. To the resulting solution was added the above-mentioned hydrated aluminum oxide and then were added 2.0 g of 34.4% solution of titanyl sulfate and 0.9 g of sodium tertiary phosphate 12-hydrate. The resulting solution was stirred for 10 minutes. The solution was evaporated to dryness. The resulting solids were heated at 1200° C. for 5 hours. Water was added to the heat-treated product to dissolve free sulfate. Insoluble solids were filtered off, washed with water, and finally dried. Thus, there was obtained the desired flaky aluminum oxide.

The thus obtained flaky aluminum oxide was examined by X-ray diffractometry. The diffraction pattern had only peaks attributable to aluminum oxide (corundum). It was found by chemical analysis that the flaky aluminum oxide contains titanium oxide in an amount of 0.9%. Observation by an optical microscope and an electron microscope revealed that the flaky aluminum oxide has a particle diameter of 3–16 µm and a thickness of about 0.2 µm and is free from crystal twinning. When dispersed into water by stirring, the flaky aluminum oxide produced a smooth streamline which is a sign of good dispersibility.

Comparative Examples

Comparative Example 1

A powder mixture was prepared by milling for 30 minutes from 111.9 g of aluminum sulfate 18-hydrate, 71.6 g of anhydrous sodium sulfate, and 53.4 g of sodium carbonate. The powder mixture was heated at 1000° C. for 1 hour. Water was added to the heated product to dissolve free sulfate. Insoluble solids were filtered off, washed with water, and finally dried. Thus, there was obtained aluminum oxide powder.

The thus obtained aluminum oxide was examined by X-ray diffractometry. The diffraction pattern had only one peak attributable to aluminum oxide (corundum). Observation by an optical microscope and an electron microscope revealed that the aluminum oxide has a particle diameter smaller than 5 µm and a thickness of about 0.3 µm, with the aspect ratio being small. When dispersed into water by stirring, the aluminum oxide powder did not produce any streamline. In addition, crystal twinning and aggregation were noticed by observation by an optical microscope and an electron microscope.

Comparative Example 2

A powder mixture was prepared by milling for 30 minutes from 111.9 g of aluminum sulfate 18-hydrate, 57.3 g of anhydrous sodium sulfate, 46.9 g of potassium sulfate, 0.34 g of titanium oxysulfate pentahydrate, 0.45 g of sodium tertiary phosphate 12-hydrate, and 53.4 g of sodium carbonate. The powder mixture was heated at approximately 1200° C. for 5 hours. Water was added to the heated product to dissolve free sulfate. Insoluble solids were filtered off, washed with water, and finally dried. Thus, there was obtained aluminum oxide powder.

The thus obtained aluminum oxide was examined by X-ray diffractometry. The diffraction pattern had only one peak attributable to aluminum oxide (corundum). Observation by an optical microscope and an electron microscope revealed that the aluminum oxide greatly fluctuates in diameter and thickness and contains many aggregates. In addition, it was poor in dispersibility.

Comparative Example 3

In 300 ml of deionized water were dissolved 111.9 g of aluminum sulfate 18-hydrate, 57.3 g of anhydrous sodium sulfate, and 46.9 g of potassium sulfate by heating above 60° C. The resulting solution is designated as the aqueous solution (a').

In 150 ml of deionized water was dissolved 53.4 g of sodium carbonate. The resulting solution is designated as the aqueous solution (b').

The aqueous solution (b') was added with stirring to the aqueous solution (a') kept at about 60° C. Stirring was continued for 15 minutes. The resulting gel was evaporated to dryness, and the dried product was heated to 1200° C. for 5 hours. Water was added to the heated product to dissolve free sulfate. Insoluble solids were filtered off, washed with water, and finally dried. Thus, there was obtained aluminum oxide powder.

The thus obtained aluminum oxide was examined by X-ray diffractometry. The diffraction pattern had only peaks attributable to aluminum oxide (corundum). Observation by an optical microscope and an electron microscope revealed that the aluminum oxide is in the form of platy particle, having a diameter of 5–30 µm and a thickness of about 1 µm and contains crystal twinning and aggregation remarkably. When dispersed into water by stirring, the aluminum oxide powder did not produce any streamline because of poor dispersibility.

Comparative Example 4

In 300 ml of deionized water were dissolved 111.9 g of aluminum sulfate 18-hydrate, 57.3 g of anhydrous sodium sulfate, and 46.9 g of potassium sulfate by heating above 60° C. To the resulting solution was added 1.0 g of 34.4% solution of titanyl sulfate without heating. The resulting solution is designated as the aqueous solution (a').

In 150 ml of deionized water was dissolved 54.0 g of sodium carbonate. The resulting solution is designated as the aqueous solution (b').

The aqueous solution (b') was added with stirring to the aqueous solution (a') kept at about 60° C. Stirring was contained for 15 minutes. The resulting gel was evaporated to dryness, and the dried product was heated at 1200° C. for 5 hours. Water was added to the heated product to dissolve free sulfate. Insoluble solids were filtered off, washed with water, and finally dried. Thus, there was obtained aluminum oxide powder.

The thus obtained aluminum oxide was examined by X-ray diffractometry. The diffraction pattern had only one peak attributable to aluminum oxide (corundum). It was found by chemical analysis that the aluminum oxide contains titanium oxide in an amount of 0.9%. Observation by an optical microscope and an electron microscope revealed that the aluminum oxide has a particle diameter of 5–20 µm and a thickness of about 1.0 µm. This thickness is much greater than that of the aluminum oxide prepared by adding a phosphoric compound.

Comparative Example 5

In 300 ml of deionized water were dissolved 111.9 g of aluminum sulfate 18-hydrate, 57.3 g of anhydrous sodium sulfate, and 46.9 g of potassium sulfate by heating above 60° C. The resulting solution is designated as the aqueous solution (a').

In 150 ml of deionized water were dissolved 0.45 g of sodium tertiary phosphate 12-hydrate and 53.4 g of sodium carbonate. The resulting solution is designated as the aqueous solution (b').

The aqueous solution (b') was added with stirring to the aqueous solution (a') kept at about 60° C. Stirring was continued for 15 minutes. The resulting gel was evaporated to dryness, and the dried product was heated at 1200° C. for 5 hours. Water was added to the heated product to dissolve free sulfate. Insoluble solids were filtered off, washed with water, and finally dried. Thus, there was obtained aluminum oxide powder.

The thus obtained aluminum oxide was examined by X-ray diffractometry. The diffraction pattern had only peaks attributable to aluminum oxide (corundum). Observation by an optical microscope and an electron microscope revealed that the aluminum oxide has a particle diameter of 5–20 µm and a thickness of about 0.2 µm and contains crystal twinning and aggregation remarkably. When dispersed into water by stirring, the aluminum oxide powder did not produce any streamline because of poor dispersibility.

Comparative Example 6

In 300 ml of deionized water were dissolved 111.9 g of aluminum sulfate 18-hydrate, 57.3 g of anhydrous sodium sulfate, and 46.9 g of potassium sulfate by heating above 60° C. To the resulting solution was added 2.25 g of 34.4% solution of titanyl sulfate. The resulting solution is designated as the aqueous solution (a').

In 150 ml of deionized water were dissolved 4.5 g of sodium tertiary phosphate 12-hydrate and 53.7 g of sodium carbonate. The resulting solution is designated as the aqueous solution (b').

The aqueous solution (b') was added with stirring to the aqueous solution (a') kept at about 60° C. Stirring was continued for 15 minutes. The resulting gel was evaporated to dryness, and the dried product was heated at 1200° C. for 5 hours. Water was added to the heated produce to dissolve free sulfate. Insoluble solids were filtered off, washed with water, and finally dried. Thus, there was obtained aluminum oxide powder.

The thus obtained aluminum oxide was found by chemical analysis to contain 4.5 % of titanium oxide. Observation by an optical microscope and an electron microscope revealed that the aluminum oxide contains no flaky particles.

Table 1 shows the conditions under which the process was carried out in Examples 1 to 6 and Comparative Examples 1 to 6.

Shape and Dispersibility:

Table 2 shows the shape and dispersibility of the samples of flaky aluminum oxide obtained in Examples 1 to 6 and Comparative Examples 1 to 6.

| Example (Comparative Example) | Particle diameter (µm) | Thickness (µm) | Aspect ratio | Twinning and Aggregation | Duration of streamline (sec)*[1] |
|---|---|---|---|---|---|
| 1 | 3–16 | 0.2 | 45 | No | 85 |
| 2 | 4–21 | 0.2 | 60 | No | 80 |
| 3 | 5–22 | 0.2 | 65 | No | 71 |
| 4 | 5–20 | 0.2 | 60 | No | 75 |
| 5 | 4–18 | 0.2 | 55 | No | 70 |
| 6 | 3–16 | 0.2 | 50 | No | 77 |
| (1) | ≦5 | 0.3 | x | Yes | 0 |
| (2) | x | x | x | Yes | 16 |
| (3) | 5–30 | 1.0 | x | Yes | 21 |
| (4) | 5–20 | 1.0 | 13 | Yes | 23 |
| (5) | 5–20 | 0.2 | x | Yes | 25 |
| (6) | ≦4 | x | x | Yes | 0 |

*[1]The sample is dispersed and stirred in water, and time required for the streamline of the sample to disappear is measured. The longer the duration, the better the dispersibility of the sample, with particles remaining dispersed in water without aggregation.
x Not measurable.

Production of pearlescent pigment:

Example 7

The flaky aluminum oxide (20 g) obtained in Example 1 was suspended in 400 ml of deionized water. To the resulting suspension (kept at about 65° C.) was added a solution containing 125 g of $TiCl_4$ per liter at a rate of 0.6 ml/min. Simultaneously a 10% solution of NaOH was added to keep the pH at 2.5. The addition of the $TiCl_4$ solution was stopped when the resulting product took on a silvery color. The suspending solids were filtered off, washed with water, and dried. Finally, the dried solids were calcined at 850° C. to give a highly whitish and glossy pearlescent pigment.

Example 8

The flaky aluminum oxide (20 g) obtained in Example 2 was suspended in 400 ml of deionized water. To the resulting suspension (kept at about 75° C.) was added a 10% solution

| | | Conditions of Preparation | | | |
|---|---|---|---|---|---|
| Example (Comparative Example) | Method | Mineralizer/ Aluminum salt (molar ratio) | $TiO_2/Al_2O_3$ (wt. %) | $P_2O_5/Al_2O_3$ (wt. %) | Type of Reaction |
| 1 | Simultaneous dropping | 4.0 | 1.0 | 0.5 | wet process |
| 2 | Simple addition | 4.0 | 1.0 | 0.5 | wet process |
| 3 | Simple addition | 4.0 | 3.0 | 0.5 | wet process |
| 4 | Simple addition | 4.0 | 1.0 | 1.5 | wet process |
| 5 | Simple addition | 4.0 | 0.5 | 0.5 | wet process |
| 6 | Hydrolysis | 2.0 | 1.0 | 0.5 | wet process |
| (1) | — | 3.0 | 0 | 0 | dry process |
| (2) | — | 4.0 | 0.6 | 0.5 | dry process |
| (3) | Addition | 4.0 | 0 | 0 | wet process |
| (4) | Addition | 4.0 | 1.0 | 0 | wet process |
| (5) | Addition | 4.0 | 0 | 0.5 | wet process |
| (6) | Addition | 4.0 | 5.0 | 2.5 | wet process | of NaOH to adjust the suspension to pH 9.0. After 10 minutes, 40 ml of a solution containing 36 g of SnCl$_4$ per liter was added at a rate of 0.6 ml/min. Simultaneously, a 10% solution of NaOH was added to keep the pH at 1.9. After 15 minutes, a solution containing 125 g of TiCl$_4$ per liter was added at a rate of 0.6 ml/min. Simultaneously, a 10% solution of NaOH was added to keep the pH at 1.9. The addition of the TiCl$_4$ solution was stopped when the resulting product took on a silvery color. The suspending solids were filtered off, washed with water, and dried. Finally, the dried solids were calcined at 850° C. to give a highly whitish and glossy pearlescent pigment. Examination by X-ray diffractometry revealed that all the titanium oxide in this pigment is of rutile type.

Example 9

The flaky aluminum oxide (20 g) obtained in Example 5 was suspended in 400 ml of deionized water. To the resulting suspension (kept at about 75° C.) was added 220 ml of a 20% solution of iron nitrate 9-hydrate at a rate of 1.0 ml/min. Simultaneously, a 10% solution of NaOH was added to keep the pH at 3.0. The suspending solids were filtered off, washed with water, and dried. Finally, the dried solids were calcined at 850° C. to give a reddish brown pearlescent pigment having a golden interference color.

The following examples demonstrate the application of the pearlescent pigment to paint, plastic composition, and printing ink.

Example 10

A base coat paint for automobiles was prepared according to the following formulation.

| <Base coat system> Acrylic-melamine resin system | |
|---|---|
| "Acrydic 47-712"* | 70 pbw |
| "Superbekkamine G821-60"** | 30 pbw |
| Toluene | 30 pbw |
| Ethyl acetate | 50 pbw |
| n-Butano | 110 pbw |
| Solvesso #150 | 40 pbw |

*Acrylic resin from Dainippon Ink & Chemicals, Inc.
**Melamine resin from Dainippon Ink & Chemicals, Inc.

The above acrylic-melamine resin system (100 pbw) was incorporated with 20 pbw of the flaky aluminum oxide or pearlescent pigment obtained in Examples 1 to 9. The resulting compound was diluted with a thinner so that the resulting paint has an adequate consistency for spraying. (12-15 seconds, Ford cup #4) This paint was applied to a substrate by spraying to form a base coat layer.

The base coated layer was coated further with a colorless top clear coat paint, which was prepared according to the following formulation.

| <top clear coat system> | |
|---|---|
| "Acrydic 44-179" | 14 pbw |
| "Superbekkamine L117-60" | 6 pbw |
| Toluene | 4 pbw |
| MIBK | 4 pbw |
| Butyl cellosolve | 3 pbw |

The top coating was exposed to air at 40° C. for 30 minutes and then cured at 135° C. for 30 minutes

Example 11

A base coat for automobiles was prepared according to the following formulation.

| <Base coat system> | |
|---|---|
| "Dynapol H-700" *1 | 25.2 g |
| "Mapranal MF-650" *2 | 2.7 g |
| "Cellulose acetobutyrate 531.1" *3 | 15.5 g |
| "Irgarol TZ-6" | 1.1 g |
| Ethyl acetate | 23.3 g |
| Xylene | 11.6 g |
| Solvesso 150 | 11.6 g |
| C.I. Pigment Red 177 | 4.5 g |
| Flaky aluminum oxide or pearlescent pigment obtained in Examples 1 to 9 | 4.5 g |

*1 A 60% solution of polyester resin in Solvesso 150, from Dynanit Nobel.
*2 A 55% solution of melamine resin in butanol, from Hoechst.
*3 A 25% solution in a 1:2 mix of xylene butyl acetate, from Eastman Chemical International.
*4 A catalyst based on mineral oil and carboxylate, from Ciba-Geigy.

The above-listed components were mixed for 96 hours using a ball mill, so that the pigments were thoroughly dispersed into the lacquer vehicle. The resulting composition was diluted with a mixed solvent of butyl acetate, xylene, and solvesso 150 to give a paint having a consistency of about 18 seconds (at 20° C.) according to DIN4. The paint was applied to a metal plate. After exposure to air at about 40° C. for 2 minutes, the base coat was further coated with a colorless top coat paint, which was prepared according to the following formulation.

| <Top clear coat system> | |
|---|---|
| "Viacryl VC-373" *1 | 58.3 g |
| "Maprenal MF-590" *2 | 27.3 g |
| Silicone oil *3 | 1.0 g |
| "Tinuvin 900" *4 | 1.0 g |
| Xylene | 1.0 g |
| "Solvesso 150" | 5.4 g |
| Ethylene glycol acetate | 3.0 g |

*1 A 60% solution of acrylic resin in xylene, from Vianora.
*2 A 55% solution of melamine resin in butanol, from Hoechst.
*3 A 1% solution in xylene, from Bayer.
*4 A benzotriazole derivative from Ciba-Geigy.

The top coating was exposed to air at 40° C. for 30 minutes and then cured at 135° C. for 30 minutes.

Example 12

This example demonstrates the application of the pearlescent pigment to the coloring of plastics. An injection molding compound (in pellet form) was prepared by dry blending according to the following formulation.

| Polyethylene resin (pellets) | 100 pbw |
|---|---|
| Flaky aluminum oxide or pearlescent pigment obtained in Examples 1 to 9 | 1 pbw |
| Zinc stearate | 0.2 pbw |
| liquid paraffin | 0.1 pbw |

Example 13

This example demonstrates the application of the pearlescent pigment to a gravure printing ink, which was prepared according to the following formulation.

| | |
|---|---|
| CCST medium *1 | 10 pbw |
| Flaky aluminum oxide or pearlescent pigment obtained in Examples 1 to 9 | 8 pbw |

*1 Nitrocellulose resin, from Toyo Ink.

The thus obtained ink was diluted with a solvent ("NC102" from Toyo Ink) so that the resulting ink had a consistency of 20 sec, Zahn cup No. 3.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Flaky aluminum oxide containing therein titanium oxide in an amount of about 0.1–4 wt. %, based on the aluminum oxide.

2. Flaky aluminum oxide according to claim 1, comprising particles having an average particle diameter of about 5–60 μm, a thickness less than about 1 μm, and an aspect ratio greater than about 20.

3. A pearlescent pigment comprising particles of a flaky aluminum oxide containing therein titanium oxide in an amount of about 0.1–4 wt. %, based on the aluminum oxide, and a metal oxide coating formed on the surface of said particles.

4. A pearlescent pigment according to claim 3, wherein the metal oxide is a titanium oxide.

5. A paint, plastic, ink, cosmetic, or glaze composition comprising a flaky aluminum oxide containing therein titanium oxide in an amount of about 0.1–4 wt. %, based on the aluminum oxide.

6. A paint, plastic, ink, cosmetic, or glaze composition comprising a pearlescent pigment which comprises a flaky aluminum oxide containing therein titanium oxide in an amount of about 0.1–4 wt. %, based on the aluminum oxide, and containing thereon a layer of a metal oxide.

7. A paint, plastic, ink, cosmetic, or glaze composition according to claim 6, wherein the metal oxide is a titanium oxide.

8. A process for producing flaky aluminum oxide, comprising preparing (a) an aqueous solution of at least one water-soluble aluminum salt and at least one titanium salt and (b) an aqueous solution of at least one alkali carbonate in an amount approximately equivalent to said water-soluble aluminum salt and titanium salt in said aqueous solution (a), uniformly dissolving at least one alkali metal sulfate and phosphoric acid or a phosphate in either aqueous solution (a) or aqueous solution (b), mixing said aqueous solutions (a) and (b) to give a suspension or gel containing hydrolyzates, drying the suspension or gel by evaporation, and molten-salt treating the dried product by heating to give a solid product, and optionally water washing, filtering, and drying.

9. A process according to claim 8, wherein the molten salt treatment is conducted at 900°–1400° C.

10. A process for producing flaky aluminum oxide, comprising adding dropwise a solution of at least one water-soluble aluminum salt and a solution of at least one alkali carbonate simultaneously to water in such a way that the former is approximately chemically equivalent to the latter, thereby forming a suspension of hydrated aluminum hydroxide, adding said suspension or solids filtered out from said suspension to an aqueous solution of at least one alkali metal sulfate, adding to the resulting solution a titanium salt and phosphoric acid or a phosphate to give a suspension or gel containing hydrolyzates, drying the suspension or gel by evaporation, and molten-salt treating the dried product to give a solid product, and optionally water washing, filtering, and drying.

11. A process according to claim 10, wherein the molten salt treatment is conducted at 900°–1400° C.

12. Flaky aluminum oxide produced by a process comprising preparing (a) an aqueous solution of at least one water-soluble aluminum salt and at least one titanium salt and (b) an aqueous solution of at least one alkali carbonate in an amount approximately equivalent to said water-soluble aluminum salt and titanium salt in said aqueous solution (a), uniformly dissolving at least one alkali metal sulfate and phosphoric acid or a phosphate in either aqueous solution (a) or aqueous solution (b), mixing said aqueous solutions (a) and (b) to give a suspension or gel containing hydrolyzates, drying the suspension or gel by evaporation, and molten-salt treating the dried product by heating to give a solid product, and optionally water washing, filtering, and drying.

13. Flaky aluminum oxide produced by a process comprising adding a dropwise solution of at least one water-soluble aluminum salt and a solution of at least one alkali carbonate simultaneously to water in such a way that the former is approximately chemically equivalent to the latter, thereby forming a suspension of hydrated aluminum hydroxide, adding said suspension or solids filtered out from said suspension to an aqueous solution of at least one alkali metal sulfate, adding to the resulting solution a titanium salt and phosphoric acid or a phosphate to give a suspension or gel containing hydrolyzates, drying the suspension or gel by evaporation, and molten-salt treating the dried product to give a solid product, and optionally water washing, filtering, and drying.

* * * * *